United States Patent
Potkin et al.

(10) Patent No.: US 9,989,540 B2
(45) Date of Patent: Jun. 5, 2018

(54) DIAGNOSTIC AND MONITORING SYSTEM FOR HUNTINGTON'S DISEASE

(71) Applicant: THE REGENTS OF THE UNIVERSITY OF CALIFORNIA, Oakland, CA (US)

(72) Inventors: Steven Potkin, Irvine, CA (US); Leslie Thompson, Irvine, CA (US); Zhiqun Tan, Irvine, CA (US); Charles Glabe, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days. days.

(21) Appl. No.: 14/889,142

(22) PCT Filed: May 9, 2014

(86) PCT No.: PCT/US2014/037403
§ 371 (c)(1),
(2) Date: Nov. 4, 2015

(87) PCT Pub. No.: WO2014/182972
PCT Pub. Date: Nov. 13, 2014

(65) Prior Publication Data
US 2016/0178645 A1 Jun. 23, 2016

Related U.S. Application Data

(60) Provisional application No. 61/822,237, filed on May 10, 2013, provisional application No. 61/990,697, filed on May 8, 2014.

(51) Int. Cl.
*G01N 33/68* (2006.01)
*G01N 33/50* (2006.01)

(52) U.S. Cl.
CPC ..... *G01N 33/6896* (2013.01); *G01N 33/5091* (2013.01); *G01N 2800/2835* (2013.01); *G01N 2800/52* (2013.01)

(58) Field of Classification Search
CPC ............... G01N 33/6896; G01N 33/49; G01N 33/5091; G01N 33/6845; G01N 2800/2835; G01N 2800/28; G01N 2500/10
See application file for complete search history.

(56) References Cited

U.S. PATENT DOCUMENTS

| | | |
|---|---|---|
| 4,816,567 A | 3/1989 | Cabilly et al. |
| 5,122,458 A | 6/1992 | Post et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |

FOREIGN PATENT DOCUMENTS

| | | |
|---|---|---|
| GB | 2211504 | 9/2008 |
| WO | 91/10741 | 7/1991 |
| WO | 96/33735 | 10/1996 |
| WO | 96/34096 | 10/1996 |
| WO | 97/15664 | 5/1997 |
| WO | 98/24893 | 6/1998 |

OTHER PUBLICATIONS

Zhang, L. and Bulaj, G. "Converting Peptides into Drug Leads by Lipidation," Curr Med Chem 19:1602-1618 (2012).
Apostol, et al. "A cell-based assay for aggregation inhibitors as therapeutics of polyglutamine-repeat disease and validation in *Drosophila*," Proc. Nat'l. Acad. Sci., 100(10):5950-55 (2003).
Chen & Wetzel, "Solubilization and Disaggregation of Polyglutamine Peptides," Protein Science : A Publication of the Protein Society 10, 887-891, (2001).
Chen, et al. "Selection and Analysis of an Optimized Anti-VEGF Antibody: Crystal Structure of an Affinity-matured Fab in Complex with Antigen," J. Mol. Biol. 293:865-881 (1999).
Clackson, et al., "Making antibody fragments using phage display libraries," Nature, 352: 624-628 (1991).
Fellouse, "Synthetic antibodies from a four-amino-acid code: a dominant role for tyrosine in antigen recognition," Proc. Natl. Acad. Sci. USA 101(34): 12467-12472 (2004).
Fiers, et al. "Complete Nucleotide Sequence of SV40 DNA," Nature 273: 113-120 (1978).
Fishwild, et al., "High-avidity human IgGk monoclonal antibodies from a novel strain of minilocus transgenic mice," Nature Biotechnol. 14: 845-851 (1996).
Gourlet, P., et al. "Interaction of lipophilic VIP derivatives with recombinant VIP1/PACAP and VIP2/PACAP receptors," Eur J Pharmacol 354: 105-111, (1998).
Gozes, I. and Furman, S. "VIP and Drug Design," Curr Pharm Des 9: 483-494 (2003).
Greenaway, P.J., et al. "Human cytomegalovirus DNA: BamHI, EcoRI and Pst I restriction endonuclease cleavage maps", Gene 18: 355-360 (1982).
Jakobovits, et al., "Analysis of homozygous mutant chimeric mice: Deletion of the immunoglobulin heavy-chain joining region blocks B-celldevelopment and antibody production," Proc. Natl. Acad. Sci. USA 90: 2551 (1993).
Jakobovits, et al., "Germ-line transmission and expression of a human-derived yeast artificial chromosome," Nature 362: 255-258 (1993).
Kaul, R. and Balaram, P. "Stereochemical Control of Peptide Folding," Bioorg Med Chem 7:105-117 (1999).

(Continued)

*Primary Examiner* — Robert C Hayes
(74) *Attorney, Agent, or Firm* — Kaplan IP Law, P.C.; Jonathan M. Kaplan

(57) ABSTRACT

The invention provides assays that identify Huntington's disease and monitor the progression and severity of conditions associated with variant Huntingtin protein (Httn). In particular, the invention provides assays that monitor the severity and progression of Huntington's Disease as well as predict the onset of symptoms. The invention also provides assays for identifying drugs for treating Huntington's disease.

17 Claims, 4 Drawing Sheets

(56) References Cited

OTHER PUBLICATIONS

Kayed, et al., "Common Structure of Soluble Amyloid Oligomers Implies Common Mechanism of Pathogenesis," Science 300(5618):486-9 (2003).
Kohler, et al. "Continuous Cultures of fused cells secreting antibody of predefined specificity," Nature 256: 495 (1975).
Lee, et al., "Bivalent antibody phage display mimics natural immunoglobulin," J. Immunol. Methods 284(1-2): 119-132 (2004).
Lee, et al., "High-affinity Human Antibodies from Phage-displayed Synthetic Fab Libraries with a Single Framework Scaffold," J. Mol. Biol. 340(5): 1073-1093 (2004).
Lonberg and Huszar, "Human Antibodies from Transgenic Mice," Intern. Rev. Immunol. 13: 65-93 (1995).
Lonberg, et al., "Antigen-specific human antibodies from mice comprising four distinct genetic modifications," Nature 368: 856-859 (1994).
Marks, et al., "By-passing Immunization Human Antibodies from V-gene Libraries Displayed on Phage," J. Mol. Biol. 222: 581-597 (1991).
Marks, et al., "By-passing Immunization: Building High Affinity Human Antibodies by Chain Shuffling," Bio. Technology 10: 779-783 (1992).
Miller, et al. "Ubiquitin-interacting motifs inhibit aggregation of polyQ-expanding huntingtin," J Biol Chem 282(13): 10096-10103 (2007).
Miller, et al., "Hollow core of Alzheimer's Aβ42 amyloid observed by cryoEM is relevant at physiological pH," Proc. Nat'l Acad. Sci. 107, 14128-14133 (2010).
Morrison, "Success in specification," Nature 368: 812-813 (1994).
Nestor, J.J., Jr. "The Medicinal Chemistry of Peptides," Current Medicinal Chemistry 16: 4399-4418 (2009).
Neuberger, "Generating high-avidity human mabs in mice," Nature Biotechnol. 14: 826 (1996).
Presta, et al., "Humanization of an Anti-Vascular Endothelial Growth Factor Monoclonal Antibody for the Therapy of Solid Tumors and Other Disorders," Cancer Res. 57: 4593-4599 (1997).
Shehi, et al. "Temperature-dependent, irreversible formation of amyloid fibrils by a soluble human ataxin-3 carrying a moderately expanded polyglutamine stretch (Q36)," Biochemistry 42(9): 14626-14632 (2003).
Sidhu, et al., "Phage-displayed Antibody Libraries of Synthetic Heavy Chain Complementarity Determining Regions," J. Mol. Biol. 338(2): 299-310 (2004).
Sontag, et al."Detection of Mutant Huntingtin Aggregation Conformers and Modulation of SDS-Soluble Fibrillar Oligomers by Small Molecules," Journal of Huntington's Disease 1 (2012) 127-140.
Sontag, et al.,"Exogenous delivery of chaperonin subunit fragment ApiCCT1 modulates mutant Huntingtin cellular phenotypes," Proc. Nat'l Acad. Sci. USA 110(8):3077-82 (2013).
Steffan, et al. "SUMO Modification of Huntingtin and Huntington's Disease Pathology," Science vol. 304 (2004).
Tam, et al. "The chaperonin TRiC controls polyglutamine aggregation and toxicity through subunit-specific interactions," Nat. Cell Biol. 8(10): 1155-1162 (2006).
Wanker, et al. "Membrane Filter Assay for Detection of Amyloid-like Polyglutamine-Containing Protein Aggregates," Methods in Enzymology 309, 375-386 (1999).
Weiss, et al. "Single-step detection of mutant huntingtin in animal and human tissues: A bioassay for Huntington's disease," Anal Biochem 395(1) (2009).
Zhang, et al. "Interprotofilament interactions between Alzheimer's Aβ1-42 peptides in amyloid fibrils revealed by cryoEM," Proc. Nat'l Acad. Sci. USA 106, 4653-4658 (2009).

DIAGNOSTIC AND MONITORING SYSTEM FOR HUNTINGTON'S DISEASE

PRIORITY

This application claims priority to U.S. provisional patent application Ser. No. 61/822,237, filed May 10, 2013, and U.S. provisional patent application Ser. No. 61/990,697, filed May 8, 2014, both which are incorporated herein by reference in its entirety.

This invention was made with Government support under Grant No. 5PN2EY016525-09 awarded by the National Institutes of Health. The Government has certain rights in this invention.

SEQUENCE LISTING

The instant application contains a Sequence Listing which has been submitted electronically in ASCII format and is hereby incorporated by reference in its entirety. Said ASCII copy, created on Nov. 13, 2015, is named RUCOO2US1_SL.txt and is 1,995 bytes in size.

FIELD OF THE INVENTION

The invention provides assays that identify Huntington's disease and monitor the severity of conditions associated with variant Huntingtin protein (Httn). In particular, the invention provides assays that monitor the severity, onset and progression of Huntington's Disease and its progression as well as predicting the onset of symptoms. The invention also provides assays for identifying drugs for treating Huntington's disease.

BACKGROUND

This invention was made with Government support under Grant No. EY016525 awarded by the National Institutes of Health. The Government has certain rights in this invention.

Huntington's disease (HD) is a neurodegenerative genetic disorder that affects muscle coordination and leads to cognitive decline and psychiatric problems. It typically strikes in mid-adult life. HD is the most common genetic cause of abnormal involuntary writhing movements called chorea, which is why the disease was previously called Huntington's chorea. Physical symptoms of Huntington's disease can begin at any age from infancy to old age, but usually begin between 35 and 44 years of age. Through genetic anticipation, the disease may develop earlier in life in successive generations. About 6% of cases start before the age of 21 years with an akinetic-rigid syndrome; they progress faster and vary slightly. The variant is classified as juvenile, akinetic-rigid or Westphal variant HD.

The progression of HD occurs over many years and can be divided into three stages, As HD affects everyone differently, including members of the same family, people will go through the stages at different times throughout the disease. In the early stages of HD, subtle changes in mood and other psychiatric symptoms, movement, and cognition are observed. During middle stage, affected individuals lose the ability to work, drive, and need help performing activities of Daily Living. HD patients experience difficulties with balance, swallowing, voluntary motor tasks, and a growing number of psychiatric symptoms, and dementia. Individuals will have increased difficulty organizing and prioritizing information. The behavioral symptoms will affect everyone differently, but typically manifest as irritability, aggression, depression, apathy, hallucinations and delusions.

Found primarily in the cytoplasm, Httn plays a role in numerous normal functions, including the function of microtubules, vesicular membranes, and synaptic proteins. The disease is caused by an abnormal CAG repeat expansion in the HD gene (HTT), leading to the production of an expanded polyglutamine repeat in the amino terminal domain of the Huntingtin protein (Httn). Httn in Huntington's disease typically has 40 or more polyglutamine repeats. A hallmark of HD is the propensity for the mutant protein (mHttn) to misfold and aggregate. As a result of the elongated polyglutamine repeat, neurons become dysfunctional and may die. Abnormal Httn also affects the immune cells' ability to migrate in response to injury. The mutated gene prevents appropriate response to injury and infections.

There is no accurate and inexpensive diagnostic test for HD progression using cerebral spinal fluid (CSF). Such a test would allow disease prediction, improved determination of the stage of the disease, or onset of symptoms. It would also provide an assessment of the efficacy of therapies that target mutant Huntingtin protein aggregation. Prior test methods and kits for diagnosing many diseases monitor changes in proteins or enzyme activities in body fluids from patients. These methods, however, look for posttranslational changes in proteins but do not measure the consequence of any such changes.

SUMMARY OF THE INVENTION

A critical barrier to the development of effective HD treatments is the lack of an efficient biomarker for longitudinal measurement of HD clinical symptom onset and progression, as well as methods to predict, measure and monitor target engagement of HD pathology crucial to the development of novel treatments. The invention thus provides assays to monitor the progression of HD in subjects. It further provides assays for monitoring Httn protein aggregates in samples that are analyzed during the development of therapeutic compositions for the treatment of HD. Cerebral spinal fluid (CSF) is obtained from patients. It has been surprisingly discovered that CSF from HD patients, when put in contact with cells expressing expanded polyglutamine Httn variants, or lysates or extracts from said cells, has the ability to increase aggregation of the Httn variants within the cells, lysates, or extracts. This activity, referred to as "seeding," is measured by the number of cells with aggregates and by the amount of aggregates within the cells, cellular lysates, or other cell-free compositions. The enhanced aggregation by HD CSF is quantifiable and used as a measure of disease presence, disease progression or remission, and the effects of therapeutic interventions.

The invention further provides assays for the development of new therapeutic compounds for the treatment of HD. The assays disclosed herein facilitate the development of new HD treatments by providing an accurate diagnosis of the disease stage and a method to follow the course of the illness that is quantitative and non-invasive. Clinical symptoms develop over years and change slowly and therefore are not sufficiently sensitive for the rapid assessment of disease modifying treatments. Thus, the invention facilitates the development of chemical, genetic, cellular, biological and molecular treatments. Furthermore, the assays of the invention provide a method for determining an appropriate dose range, frequency of treatment, pharmacokinetics, pharmacodynamics, and other treatment related factors. Moreover, the invention provides a simple and rapid cell-based or cell-free method of identifying compounds that may affect mHttn seeding, and thus, treatments for Huntington's disease. This method is, in some embodiments, quantitative.

Thus, the invention provides a method for monitoring the severity of Huntington's Disease (HD) in a subject, comprising exposing a first cell culture having cells that express an Httn protein variant that aggregates through its polyglutamine domain to a bodily fluid taken from said subject with HD; quantifying the Httn variant aggregates in said first cell culture; exposing a second cell culture having cells that express an Httn protein variant that aggregates through its polyglutamine domain to a negative control sample; quantifying the Httn variant aggregates in said second cell culture; comparing the quantity of variant Httn aggregates in said first and said second cell cultures; wherein a larger quantity of Httn variant aggregates in said first cell culture as compared to said quantity of aggregates in said second cell culture indicates a severity of said Huntington's Disease. In a preferred embodiment, the bodily fluid is CSF or blood plasma. In another embodiment, the methods described above and throughout this application may be used to monitor Huntington's disease in prior to a subject presenting clinical symptoms.

In a preferred embodiment, the methods disclosed herein use cells that express an Httn protein derived from an origin selected from the group consisting of adrenal tissue, neuronal tissue, connective tissue, muscle tissue, epithelial tissue, hepatic tissue, fibroblasts, lymphocytes, monocytes, macrophages, stem cells and pluripotent cells. In another preferred embodiment, the cells are derived from a mammal, reptile, amphibian, fish, insect, mold, yeast, protozoan, bacterium, or archaebacterium. In another preferred embodiment, the cells are derived from a mouse, rat, or human. In a most preferred embodiment, the cells that express said Httn variant are selected from the group consisting of PC-12 cells, RGC5 cells, and SH-SY5Y cells.

In another embodiment, the Httn protein variant expressed in the cells is a protein having at least a 90% sequence identity with SEQ ID NO:1 outside of a polyglutamine repeat within said Httn protein variant sequence.

In another embodiment, said Httn protein is expressed from a nucleic acid molecule that binds with high stringency to the DNA that expresses the Httn protein in Httl4A2.6 inducible PC-12 cells. In another embodiment, said Httn protein has at least a 90% sequence identity with the Httn variants disclosed in Apostol et al., Proc. Nat'l Acad. Sci. USA 100(10):5950-55 (2013).

In another embodiment, the quantifying step is accomplished by a technique selected from the group consisting of fluorescence microscopy, gel electrophoresis, western blot, dot blot, filter trap, XTT cell rescue, flow cytometry, ELISA, FRET, mass spectroscopy, resonant mass measurement, microfluidic imaging, Archimedes, fluorescence spectrometry, and optical density measurement. In a preferred embodiment, the quantifying step comprises the use of an antibody that specifically binds an Httn protein variant.

In another embodiment, the invention provides a method of determining the progression or regression of HD disease in a subject. This method comprises repeating the method steps described above and throughout this application one or more times to track the severity of an HD disease over time. In a preferred embodiment, the method further comprises adjusting the dose of a therapeutic compound in said subject. In another preferred embodiment, the method further comprises causing the dose of a therapeutic compound in said subject to be adjusted.

In another embodiment, the quantity of variant Httn aggregates in the first cell culture is additionally compared to the aggregates formed in a plurality of cell cultures exposed to an Httn variant having a known seeding activity at a plurality of standardized concentrations and wherein the quantity of Httn variant aggregates in the first cell culture is compared to the quantities in a standard curve of aggregates resulting from the plurality of cell cultures.

In another embodiment, the invention provides a method of determining the therapeutic efficacy of a compound for treating HD disease, comprising repeating the method described above and throughout this application one or more times to track the effect of said compound over time.

In another embodiment, the Httn protein variant is expressed from a HTT gene under the control of an inducible expression system. In another embodiment of the invention, the Httn protein variant is temperature sensitive. In another embodiment, the invention the Httn protein variant is activated by a post-translational mechanism. In another embodiment, the invention the Httn protein variant is expressed from a HTT gene under the control of a constitutive expression system.

The invention provides a cell for use in the methods described above and throughout this application. In a preferred embodiment, the cell was created by the use of recombinant DNA technology. In another embodiment, the cell used in the methods described above and throughout this application is an immortalized cell.

The invention provides a method for monitoring the severity of Huntington's Disease (HD) in a subject, comprising; exposing a first cell-free composition comprising an Httn protein variant that aggregates through its poly-glutamine domain to a bodily fluid taken from the subject with HD; quantifying the Httn variant aggregates in the first cell-free composition; exposing a second cell-free composition comprising an Httn protein variant that aggregates through its poly-glutamine domain to a negative control sample; quantifying the Httn variant aggregates in the second cell-free composition; comparing the quantity of variant Httn aggregates in the first and the second cell-free compositions; wherein a larger quantity of Httn variant aggregates in the first cell-free composition as compared to the quantity of aggregates in the second cell-free composition indicates a severity of the Huntington's Disease.

In a preferred embodiment, the first and second cell-free compositions are cell extracts. In another preferred embodiment, the first and second cell-free compositions comprise a substantially pure Httn protein variant. In a more preferred embodiment, the first and second cell-free compositions comprise an Httn peptide oligomer. In another more preferred embodiment, the first and second cell-free compositions comprise synthetic polyglutamine peptides.

In other embodiments, the bodily fluid is CSF or blood plasma.

In other embodiments, the cell extracts are from cells that express said Httn protein that are derived from an origin selected from the group consisting of adrenal tissue, neuronal tissue, connective tissue, muscle tissue, epithelial tissue, hepatic tissue, fibroblasts, lymphocytes, monocytes, macrophages, stem cells and pluripotent cells. In other embodiments, the cells are derived from a mammal, reptile, amphibian, fish, insect, mold, yeast, protozoan, bacterium, or archaebacterium. In preferred embodiments, the cells are derived from a mouse, rat, or human. In more preferred embodiments, the cells that express the Httn variant are selected from the group consisting of PC-12 cells, RGC5 cells, and SH-SY5Y cells. The invention contemplates other cultured cells.

In some embodiments, the Httn protein variant is a protein having at least a 90% sequence identity with SEQ ID NO:1 outside of a polyglutamine repeat within said Httn protein variant sequence. In other embodiments, the Httn variant is a peptide comprising 10 or more consecutive glutamine amino acids. In a more preferred embodiment, the Httn variant further comprises a fluorescence tag. In a more preferred embodiment, the fluorescence tag is green fluorescence protein (GFP). In another embodiment, the Httn protein variant is a synthetic peptide that has at least a 90% sequence identity with SEQ ID NO:1 or SEQ ID NO:2. In a most preferred embodiment, the Httn variant comprises SEQ ID NO:1 or SEQ ID NO:2. In another most preferred embodiment, the Httn variant is mHttex1-GFP. In another embodiment, the Httn protein variant comprises an enzymatic tag. Preferred enzymatic tags include alkaline phosphotase (AP) or horse radish peroxidase (HRP). In more preferred embodiments, the Httn variant is mHttex1-AP or mHttex1-HRP.

In the other embodiments, the Httn variant is a recombinant protein or a synthetic peptide comprising polyglutamine containing at least 37 repeats of glutamine residue. In more preferred embodiments, the cell-free assay will include the mHttn variant, biospecimens, and a fluorescent dye that binds aggregate fibrils. In most preferred embodiments, the fluorescent dye is thioflavin S, thioflavin T, or Congo red.

In other embodiments, the cell-free methods of the invention use a quantifying step selected from the group consisting of fluorescence microscopy, gel electrophoresis, western blot, dot blot, filter trap, XTT cell rescue, flow cytometry, ELISA, FRET, mass spectroscopy, resonant mass measurement, microfluidic imaging, Archimedes, fluorescence spectrometry, and optical density measurement. In a more preferred embodiment, the quantifying step comprises the use of an antibody that specifically binds an Httn protein variant.

The invention provides a method of determining the progression or regression of HD disease in a subject, comprising repeating the methods described herein one or more times to track said severity of said HD disease over time. In a preferred embodiment, the method further comprises the step of beginning treatment with a therapeutic compound or causing the dose of a therapeutic compound in said subject to be adjusted. In another preferred embodiment, the invention provides a method of determining the therapeutic efficacy of a compound for treating HD disease, comprising repeating the methods described herein one or more times to track the effect of said compound over time.

In another embodiment, the quantity of variant Httn aggregates in the first cell-free composition is additionally compared to the aggregates formed in a plurality of cell-free compositions comprising an Httn variant having a known seeding activity at a plurality of standardized concentrations and wherein the quantity of Httn variant aggregates in the first cell-free composition is compared to the quantities in a standard curve of aggregates resulting from the plurality of cell-free compositions.

In other embodiments, the invention provides a method for identifying a therapeutic compound for treating Huntington's Disease (HD), comprising; exposing a cell-free composition comprising an Httn protein variant that aggregates through its poly-glutamine domain to a test compound; exposing said cell-free composition with said test compound to an Httn variant that has seeding activity; quantifying the Httn variant aggregates in said cell-free composition comprising said test compound and said Httn variant; comparing the quantity of variant Httn aggregates in said first cell-free composition comprising said test compound with a second cell-free composition comprising said Httn variant but lacking said test compound; and determining whether said test compound effected the quantity of Httn aggregates in said first cell-free composition. In additional embodiments, the method for identifying a therapeutic compound described above uses an extract from cells that express an Httn peptide. In another embodiment, the cell-free composition uses a synthetic Httn protein. In a preferred embodiment, the Httn protein has the sequence of SEQ ID NO:2. In other embodiments, the invention provides a medicament identified by the methods disclosed herein.

In another embodiment of the assay to identify a therapeutic compound, the quantity of variant Httn aggregates in the first cell-free composition is additionally compared to the aggregates formed in a plurality of cell-free compositions comprising an Httn variant having a known seeding activity at a plurality of standardized concentrations and wherein the quantity of Httn variant aggregates in the first cell-free composition is compared to the quantities in a standard curve of aggregates resulting from the plurality of cell-free compositions.

The invention provides cell-free compositions for use in the assays described herein comprising cellular extracts or a synthetic Httn variant proteins.

The invention provides a kit for monitoring the severity of Huntington's Disease (HD) in a subject, comprising a cell culture having cells that express an Httn protein variant that aggregates through its polyglutamine domain, or alternatively, a cell-free composition comprising an Httn variant, a test for quantifying the Httn variant aggregates in the cell culture, and instructions for its use. In a preferred embodiment, the kit further comprises a receptacle for processing CSF samples. In another preferred embodiment, the kit further comprises a negative control sample. In another preferred embodiment, the kit further comprises a positive control sample. In another preferred embodiment, the kit further comprises standards of known Httn aggregation activity.

DETAILED DESCRIPTION OF THE INVENTION

Figure 1A:
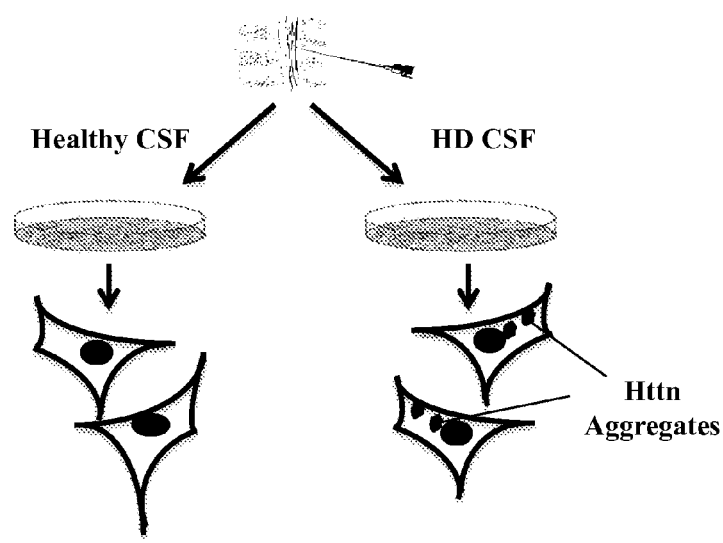
FIG. 1. (a) Schematic drawing of the HD CSF assay (whole cell). CSF is taken from a subject and exposed to cells in vitro that express expanded polyglutamine Httn variants. Where the CSF was from a subject that had HD, the Httn variants formed aggregates in a larger percentage of cells and formed a larger quantity of aggregates that are measured using standard assays, including immunoassays and fluorescent assays. (b) Schematic drawing of cell-free assay.
Figure 1B:
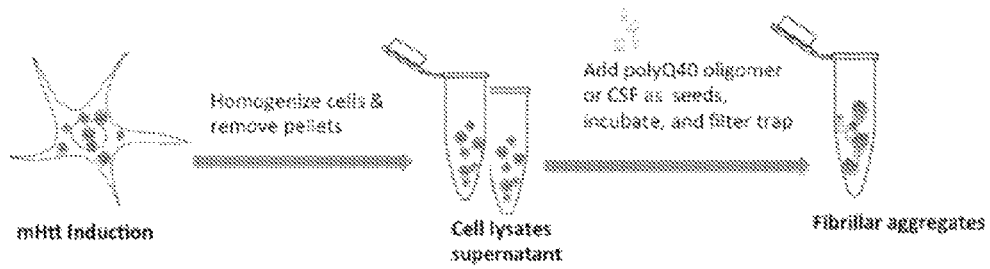

The inventions described herein provide a new method for rapidly evaluating HD in patients and during the process of drug development. In particular, the invention provides assays that monitor the severity of Huntington's Disease as well as predicting the onset of symptoms.

"HTT" is the gene that encodes Huntingtin, the protein that, in certain forms, causes Huntington's disease. Non-diseased individuals have at the 5' end a repeating CAG sequence coding for the amino acid glutamine. This region is called a trinucleotide repeat. Normal persons have a CAG repeat count of between seven and 35 repeats. Higher repeat numbers are responsible for Huntington's disease. These aberrant polyglutamine domains cause aggregation of the Huntingtin protein. HTT, as used herein, refers to a family of gene sequences that vary based upon the number of CAG repeats.

Httn refers to Huntingtin, a protein encoded by HTT and has an N-terminal polyglutamine domain that varies from individual to individual. Httn, as used herein, refers to a family of proteins that vary based upon the size of the polyglutamine domain. mHttn refers to mutant Httn proteins.

"Antibodies" (Abs), "immunoglobulins" (Igs) and monoclonal antibodies (mAbs) refer to glycoproteins having similar structural characteristics. Antibodies that are disclosed herein exhibit binding specificity to specific antigens.

"Homologs" are bioactive molecules that are similar to a reference molecule at the nucleotide sequence, peptide sequence, functional, or structural level. Homologs may include sequence derivatives that share a certain percent identity with the reference sequence. Thus, in one embodiment, homologous or derivative sequences share at least a 70 percent sequence identity. In a preferred embodiment, homologous or derivative sequences share at least an 80 or 85 percent sequence identity. In a more preferred embodiment, homologous or derivative sequences share at least about an 86, 87, 88, 89, 90, 91, 92, 93, 94, 95, 96, 97, 98, or 99 percent sequence identity. Homologous or derivative nucleic acid sequences may also be defined by their ability to remain bound to a reference nucleic acid sequence under high stringency hybridization conditions. Homologs having a structural or functional similarity to a reference molecule may be chemical derivatives of the reference molecule. Methods of detecting, generating, and screening for structural and functional homologs as well as derivatives are known in the art.

"Hybridization" generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al, Current Protocols in Molecular Biology, Wiley Interscience Publishers, (1995).

An "individual," "subject" or "patient" is a vertebrate. In certain embodiments, the vertebrate is a mammal. Mammals include, but are not limited to, primates (including human and non-human primates) and rodents (e.g., mice, hamsters, guinea pigs, and rats). In certain embodiments, a mammal is a human. A "control subject" refers to a healthy subject who has not been diagnosed as having a disease, dysfunction, or condition that has been identified in an individual, subject, or patient. A control subject does not suffer from any sign or symptom associated with the disease, dysfunction, or condition.

A "medicament" is an active drug that has been manufactured for the treatment of a disease, disorder, or condition.

"Nucleic acids" are any of a group of macromolecules, either DNA, cDNA, RNA, or variants thereof, that carry genetic information that may direct cellular functions. The nucleic acids used in the inventions described herein may be single-stranded, double-stranded, linear or circular.

As used herein, the term "peptide" is any peptide comprising two or more amino acids. The term peptide includes short peptides (e.g., peptides comprising between 2-14 amino acids), medium length peptides (15-50) or long chain peptides (e.g., proteins). The terms peptide, medium length peptide and protein may be used interchangeably herein. As used herein, the term "peptide" is interpreted to mean a polymer composed of amino acid residues, related naturally occurring structural variants, and synthetic non-naturally occurring analogs thereof linked via peptide bonds, related naturally-occurring structural variants, and synthetic non-naturally occurring analogs thereof. Synthetic peptides can be synthesized, for example, using an automated peptide synthesizer. Peptides can also be synthesized by other means such as by cells, bacteria, yeast or other living organisms. Peptides may contain amino acids other than the 20 gene-encoded amino acids. Peptides include those modified either by natural processes, such as processing and other post-translational modifications, but also by chemical modification techniques. Such modifications are well described in basic texts and in more detailed monographs, and are well-known to those of skill in the art. Modifications occur anywhere in a peptide, including the peptide backbone, the amino acid side-chains, and the amino or carboxyl termini.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µl/ml), 0.1% SDS, and 10% dextran sulfate at 42° C., with a 10 minute wash at 42° C. in 0.2×SSC (sodium chloride/ sodium citrate) followed by a 10 minute high-stringency wash consisting of 0.1×SSC containing EDTA at 55° C.

The invention provides, for the first time, rapid and accurate methods for diagnosing the severity or progression of HD. The methods are quantitative and rely on only small amounts of CSF or blood for testing. The methods of the invention may be used in both clinical and research settings. The ability to diagnose the severity and progression of HD will enable physicians and other caregivers to best optimize HD therapeutic delivery and to evaluate other patient care needs. Likewise, the methods disclosed herein may be used for rapid or automated screening and evaluation of compounds that are being investigated as HD treatments.

It has been surprisingly found that the methods disclosed are effective at low concentrations of CSF. Thus, in some embodiments, the CSF used in the methods are not diluted or diluted at about one of the following ratios: 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20. In other embodiments, the dilution may fall within about one of the following ranges 1:20-1:30, 1:30-1:40, 1:40-1:50, 1:50-1:60, 1:60-1:70, 1:70-1:80, 1:80-1:90, 1:90-1:100, 1:100-1:200, 1:200-1:300, 1:300-1:400, 1:400-1:500, 1:500-1:600, 1:600-1:700, 1:700-1:800, 1:800-1:900, or 1:900-1:1000. In yet other embodiments, CSF may be used at a 10n-fold dilution wherein n is 3, 4, 5, 6, 7, 8, 9 or 10.

In some embodiments, the invention contemplates using positive controls in the Httn aggregation assay. Such embodiments include CSF from known HD patients. Other embodiments include Httn proteins that were isolated from HD CSF. Other embodiments include Httn prepared from cells that have been modified or selected to produce the Httn proteins. Other embodiments include synthetic Httn proteins or Httn-like peptides that cause or trigger Httn aggregation via polyglutamine domains. In other embodiments, the invention contemplates negative controls. Negative controls may be derived from non-HD CSF preparations or may be saline, solvents, diluents, or water as is known in the art.

In some embodiments, the methods disclosed herein are used to optimize the dose of a therapeutic treatments used to treat HD. Examples of therapeutic treatments can include small molecules, biologics, nucleic acids, cells, and viruses. Because the method is rapid, quantitative, and therapeutic, the progression or regression of HD can be monitored at time points chosen by a clinician or researcher. Likewise, the methods of the invention may be used to determine the efficacy of said therapeutic treatments. Treatment efficacy may be measured as part of a therapeutic regimen or during the process of treatment development, clinical trials, or other drug evaluations. In some embodiments, the methods further comprise causing a dose of a therapeutic compound to be initiated or adjusted. Causing a dose to be adjusted can be accomplished directly by adjusting the dosage prescribed or administered to a subject. Alternatively, causing a dose to be adjusted would include communicating to a health professional or patient information that results in a dose initiation or adjustment. This communication could be oral, written, electronic or facsimile. Likewise, in other embodiments, the methods further comprise recommending that a dose of a therapeutic compound to be initiated or adjusted. Recommending that a dose to be initiated or adjusted would include communicating to a health professional or patient information that indicates a dose initiation or adjustment. This communication could be oral, written, electronic or facsimile.

In some embodiments, it may be required to collect CSF. Methods for collecting CSF are well known in the art. One embodiment contemplates lumbar puncture with fluid collection. Other embodiments contemplate alternative methods of CSF collection that may be necessary, e.g., if the subject has a back deformity or an infection. Thus another embodiment contemplates cisternal puncture. This method uses a needle placed below the occipital bone, usually done with fluoroscopy. In another embodiment, ventricular puncture is used. This technique may be used with subjects having possible brain herniation. A hole is drilled in the skull, and a needle is inserted directly into one of the brain's ventricles. In yet another embodiment, CSF may also be collected from a tube that's already placed in the fluid, such as a shunt or a ventricular drain.

The invention contemplates using any cells that are capable of expressing Httn and displaying aggregates in response to HD CSF. Cell culture, cell line cultures, and tissue culture are known in the art. Cells can be isolated from tissues for ex vivo culture in several ways. Cells can be purified from blood. Mononuclear cells can be released from soft tissues by enzymatic digestion with enzymes such as collagenase, trypsin, or pronase, which break down the extracellular matrix. Alternatively, pieces of tissue can be placed in growth media, and the cells that grow out are available for culture.

Cells that are cultured directly from a subject are known as primary cells. With the exception of some derived from tumors, most primary cell cultures have limited lifespan. Primary cell cultures may be immortalized by techniques known in the art. An established or immortalized cell line has acquired the ability to proliferate indefinitely. Examples of know immortalization methods include isolation from a naturally occurring cancer, spontaneous or induced random mutagenesis, introduction of a viral gene or genome, artificial expression of key proteins, e.g. telomerase, and hybridoma technology. Additionally, unicellular organism as disclosed herein may be used for the assay methods described herein.

The invention provides Httn variants that aggregate in the presence of HD bodily fluids such as CSF or blood. The Httn variants may be within intact cells, used in cell-free extracts, or as synthetic peptide oligomers. In a preferred embodiment, the Httn variants comprise about 10 or more consecutive glutamine amino acids. In more preferred embodiments, the Httn variants comprise about 10-20, 20-30, 30-40, 40-50, 50-60, 60-70, 70-80, 80-90, 90-100, or more than 100 consecutive glutamine amino acids. In most preferred embodiments, the Httn variants comprise the sequence of SEQ ID NO:1 or SEQ ID NO:2.

As described herein and as known in the art, the invention contemplates purified, substantially purified, and isolated Httn peptides. It also contemplates Httn peptides in cells and cell lysates. The term peptide is meant to include a string of amino acids. The amino acids in the peptides of the invention may be naturally-occurring or non-naturally-occurring. The peptides of the invention may be synthesized chemically or biologically, and can include cysteine-rich peptides, circular peptides, stapled peptides, peptides that include D- or L-amino acids and mixtures thereof, peptidomimetics, peptide-nucleic acids (PNAs), and combinations thereof.

Also contemplated within the scope of embodiments described herein are peptides that are branched or cyclic, with or without branching. Cyclic, branched and branched circular peptides result from post-translational natural processes and are also made by suitable synthetic methods. In some embodiments, any peptide product described herein comprises a peptide analog described above that is then covalently attached to an alkyl-glycoside surfactant moiety.

Also contemplated within the scope of embodiments presented herein are peptide chains that are substituted in a suitable position by the modification of the analogs claimed herein. For example, acylation is on a linker amino acid, for example, at the ε-position of Lysine, with fatty acids such as octanoic, decanoic, dodecanoic, tetradecanoic, hexadecanoic, octadecanoic, 3-phenylpropanoic acids and the like, or with saturated or unsaturated alkyl chains (Zhang, L. and Bulaj, G. (2012) Curr Med Chem 19: 1602-1618, incorporated herein by reference in its entirety).

Also contemplated within the scope of embodiments presented herein are peptide chains that are comprised of natural and unnatural amino acids or analogs of natural amino acids. As used herein, peptide and/or protein "analogs" comprise non-natural amino acids based on natural amino acids, such as tyrosine analogs, which includes para-substituted tyrosines, ortho-substituted tyrosines, and meta-substituted tyrosines, wherein the substituent on the tyrosine comprises an acetyl group, a benzoyl group, an amino group, a hydrazine, an hydroxyamine, a thiol group, a carboxy group, a methyl group, an isopropyl group, a C2-C20 straight chain or branched hydrocarbon, a saturated or unsaturated hydrocarbon, an O-methyl group, a polyether group, a halogen, a nitro group, or the like. Examples of Tyr analogs include 2,4-dimethyl-tyrosine (Dmt), 2,4-diethyl-tyrosine, O-4-allyl-tyrosine, 4-propyl-tyrosine, Ca-methyl-tyrosine and the like. Examples of lysine analogs include ornithine (Orn), homo-lysine, Ca-methyl-lysine (CMeLys), and the like. Examples of phenylalanine analogs include, but are not limited to, meta-substituted phenylalanines, wherein the substituent comprises a methoxy group, a C1-C20 alkyl group, for example a methyl group, an allyl group, an acetyl group, or the like. Specific examples include, but are not limited to, 2,4,6-trimethyl-L-phenylalanine (Tmp), O-methyl-tyrosine, 3-(2-naphthyl)alanine (Nal(2)), 3-(1-naphthyl)alanine (Nal(1)), 3-methyl-phenylalanine, 1,2,3,4-tetrahydroisoquinoline-3-carboxylic acid (Tic), fluorinated phenylalanines, isopropyl-phenylalanine, p-azido-phenylalanine, p-acyl-phenylalanine, p-benzoyl-phenylalanine, p-iodo-phenylalanine, p-bromophenylalanine, p-amino-phenylalanine, and isopropyl-phenylalanine, and the like.

Also contemplated within the scope of embodiments presented herein are peptide chains containing nonstandard or unnatural amino acids known to the art, for example, C-alpha-disubstituted amino acids such as Aib, Ca-diethyl-glycine (Deg), aminocyclopentane-1-carboxylic acid (Ac4c), aminocyclopentane-1-carboxylic acid (Ac5c), and the like. Such amino acids frequently lead to a restrained structure, often biased toward an alpha helical structure (Kaul, R. and Balaram, P. (1999) Bioorg Med Chem 7: 105-117, incorporated herein by reference in its entirety). Additional examples of such unnatural amino acids useful in analog design are homo-arginine (Har), and the like. Substitution of reduced amide bonds in certain instances leads to improved protection from enzymatic destruction or alters receptor binding. By way of example, incorporation of a Tic-Phe dipeptide unit with a reduced amide bond between the residues (designated as Tic-F[CH2-NH]^-Phe) reduces enzymatic degradation.

Also contemplated within the scope of embodiments presented herein are modifications at the amino or carboxyl terminus may optionally be introduced into the present peptides or proteins (Nestor, J. J., Jr. (2009) Current Medicinal Chemistry 16: 4399-4418). For example, the present peptides or proteins can be truncated or acylated on the N-terminus (Gourlet, P., et al. (1998) Eur J Pharmacol 354: 105-1 1 1, Gozes, I. and Furman, S. (2003) Curr Pharm Des 9: 483-494). The contents of the foregoing references are incorporated herein by reference in their entirety.

In some embodiments, the methods described herein use recombinant cells that express an HTT gene or a derivative thereof to produce an Httn protein capable of forming aggregates via the polyglutamine domain. Recombinant DNA technology is known in the art. In some embodiments, cells are transformed with expression vectors such as plasmids. In other embodiments, the vectors have one or more genetic signals, e.g., for transcriptional initiation, transcriptional termination, translational initiation and translational termination. Here, HTT sequences may be cloned in a vector so that it is expressed when properly transformed into a suitable host organism. In some embodiments, the cells used in the methods disclosed herein utilize recombinant expression systems having elements as defined below:

A "polyadenylation signal" is a signal sequence which causes cleavage at a specific site at the 3' end of a eukaryotic mRNA molecule and involves a post-transcriptional incorporation of a sequence of about 100-200 adenine nucleotides (polyA tail) at the cleaved 3' end. The polyadenylation signal may comprise the sequence AATAAA about 10-30 nucleotides upstream of the cleavage site and a sequence located downstream. Various polyadenylation elements are known such as tk polyA, SV40 late and early polyA or BGH polyA (described for example in U.S. Pat. No. 5,122,458, incorporated herein by reference).

A "promoter" refers to a polynucleotide sequence which allows and controls the transcription of the genes or sequences functionally connected to them. A promoter contains recognition sequences for binding RNA polymerase and the initiation site for transcription (transcription initiation site). A suitable functional promoter must be chosen. A variety of promoters from various sources are known to those of skill in the art. Promoters of the invention include constitutive, inducible and repressible promoters. The activity of inducible promoters is increased in response to cis or trans-acting factors or signals. Examples of inducible promoters are the jun, fos, metallothionein and heat shock promoters.

"Transcription-regulatory elements" generally refer to promoters upstream of the gene of interest to be expressed, transcription initiation and termination sites and a polyadenylation signal. Other transcription-regulatory elements include enhancers, locus control regions, and binding sites for cis or trans-acting factors.

The term "transcription initiation site" refers to a nucleic acid sequence that corresponds to the first nucleic acid residue that is transcribed into mRNA. The transcription initiation site may overlap with the promoter sequences.

The term "transcription termination site" refers to a nucleotide sequence that is normally at the 3' end of the nucleic acid sequence being transcribed and brings about the termination of transcription by RNA polymerase.

"Translation regulatory elements" comprise a translation initiation site (AUG), a stop codon and a polyA signal for each polypeptide to be expressed. In one embodiment, 5' or 3' untranslated regions of the nucleic acid sequence are added, removed, or changed in order to eliminate any potentially unsuitable additional translation initiation codons or other sequences which might affect expression at the transcription or expression level. In another embodiment, ribosomal consensus binding sites may be inserted immediately upstream of the start codon. Genes of interest encoding secreted proteins contain a signal precursor peptide which transports the synthesized polypeptide to and through the ER membrane. The signal sequence is often, but not always, located at the amino terminus of the secreted protein and may be cleaved by signal peptidases after the protein has passed through the ER membrane. The signal sequence may be native or heterologous to the gene of interest.

The terms "vector," "polynucleotide vector," "construct," and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, conjugated with transferring, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

Promoters for expressing genes of interest are known in the art. Either inducible or constitutive promoters are contemplated by the invention. Examples of suitable mammalian promoters for use in the invention include, for example, promoters from the following genes: ubiquitin/S27a promoter of the hamster (WO 97/15664), Simian vacuolating virus 40 (SV40) early promoter, adenovirus major late promoter, mouse metallothionein-I promoter, the long terminal repeat region of Rous Sarcoma Virus (RSV), mouse mammary tumor virus promoter (MMTV), Moloney murine leukemia virus Long Terminal repeat region, and the early promoter of human Cytomegalovirus (CMV). Examples of other heterologous mammalian promoters are the actin, immunoglobulin or heat shock promoter(s). In a preferred embodiment, a yeast alcohol oxidase promoter is used.

In additional embodiments, promoters for use in mammalian host cells can be obtained from the genomes of viruses such as polyoma virus, fowlpox virus (UK 2,211,504 published 5 Jul. 1989), bovine papilloma virus, avian sarcoma virus, cytomegalovirus, a retrovirus, hepatitis-B virus and Simian Virus 40 (SV40). In further embodiments, heterologous mammalian promoters are used. Examples include the actin promoter, an immunoglobulin promoter, and heat-shock promoters. The early and late promoters of SV40 are conveniently obtained as an SV40 restriction fragment which also contains the SV40 viral origin of replication. Fiers et al., Nature 273: 113-120 (1978). The immediate early promoter of the human cytomegalovirus is conveniently obtained as a HindIll E restriction fragment. Greenaway, P. J. et al., Gene 18: 355-360 (1982). The foregoing references are incorporated by reference in their entirety.

Eukaryotic expression systems employing insect cell hosts may rely on either plasmid or baculoviral expression systems. The typical insect host cells are derived from the fall army worm (*Spodoptera frugiperda*). For expression of a foreign protein these cells are infected with a recombinant form of the baculovirus *Autographa californica* nuclear polyhedrosis virus which has the gene of interest expressed under the control of the viral polyhedrin promoter. Other insects infected by this virus include a cell line known commercially as "High 5" (Invitrogen) which is derived from the cabbage looper (*Trichoplusia ni*). Another baculovirus sometimes used is the Bombyx mori nuclear polyhedorsis virus which infect the silk worm (Bombyx mori). Numerous baculovirus expression systems are commercially available, for example, from Invitrogen (Bac-N-Blue™), Clontech (BacPAK™. Baculovirus Expression System), Life Technologies (BAC-TO-BAC™), Novagen (Bac Vector System™), Pharmingen and Quantum Biotechnologies). Another insect cell host is the common fruit fly, Drosophila melanogaster, for which a transient or stable plasmid based transfection kit is offered commercially by Invitrogen (The DES™. System).

In some embodiments, cells are transformed with the Httn expression vectors. Transformation techniques for inserting new genetic material into eukaryotic cells, including animal and plant cells, are well known. Viral vectors may be used for inserting expression cassettes into host cell genomes. Alternatively, the vectors may be transfected into the host cells. Transfection may be accomplished by calcium phosphate precipitation, electroporation, optical transfection, protoplast fusion, impalefection, and hydrodynamic delivery.

In other embodiments, HTT or Httn expression and function may be subject to temperature sensitivity. Temperature sensitive mutations are identified by methods well-known in the art. Additionally, the invention contemplates regulation of the Httn variants using post-translational modifications or activations as is well-known in the art. In such embodiments, leader sequences, preprotein sequences, phosphorylation, or glycosylation may be manipulated, added or removed in order to activate the Httn proteins.

The methods described herein quantify the Httn aggregates using detection methods. In one embodiment, fluorescence microscopy assays are used to count cells that have aggregates. In a preferred embodiment, the aggregates are formed by GFP-Httn. Fluorescence, including immunofluorescence, encompass known techniques in the art that are used for light microscopy with a fluorescence microscope. In another embodiment, the technique uses an antibody to detect Httn. In a preferred embodiment, the technique uses an antibody to detect aggregated Httn. In another embodiment, immunofluorescence microscopy assays are used to count cells that have aggregates. Immunofluorescence microscopy is a widely used example of examining immunostained samples and is a specific example of immunohistochemistry that makes use of fluorophores to visualize the location of the antibodies.

The invention provides Httn variants that further comprise a fluorescence tag or dye. Fluorescent tags are well-known in the art. A "fluorescent dye" or "fluorophore" or "fluorochrome" is a fluorescent chemical compound that can re-emit light upon light excitation. Fluorescent dyes typically, but not necessarily, contain several combined aromatic groups, or plane or cyclic molecules with several π bonds. In one embodiment, the Httn variants of the invention comprise a non-protein organic fluorophore. Non-protein organic fluorophores belong to following major chemical families: xanthene derivatives including fluorescein, rhodamine, Oregon green, eosin, and Texas red; cyanine derivatives including cyanine, indocarbocyanine, indocyanine green, oxacarbocyanine, thiacarbocyanine, and merocyanine; naphthalene derivatives including dansyl and prodan derivatives; coumarin derivatives; oxadiazole derivatives including pyridyloxazole, nitrobenzoxadiazole and benzoxadiazole; pyrene derivatives including cascade blue; oxazine derivatives including Nile red, Nile blue, cresyl violet, and oxazine 170; acridine derivatives incuding proflavin, acridine orange, and acridine yellow; arylmethine derivatives including auramine, crystal violet, and malachite green; and tetrapyrrole derivatives including porphin, phthalocyanine, and bilirubin. In a preferred embodiment, the fluorescence tag is green fluorescence protein (GFP). In a most preferred embodiment, the Httn variant is mHttex1-GFP.

The invention contemplates using the assays disclosed herein for high-throughput drug screening using methods well known in the art. Httn seeding assays may, for example, be conducted using microtiter plates, molecular beacons, biological chips, centrifuges, robotics, data processing and control software, liquid handling devices, or sensitive detectors. The methods disclosed herein may be used to efficiently test hundreds, thousands, or millions of chemical or pharmacological agents for the ability to control seeding. Active Huntington's Disease therapeutic candidates are thus identified for further study.

Standard curves and individual concentrations for the Httn seeding assays may be set up for both the cell-based and cell-free assays. In some embodiments, the Httn proteins may be used at or about 1, 2, 3, 4, 5, 6, 7, 8, or $9\times10^{-9}$ molar concentrations. In other embodiments, the Httn proteins may be used at or about 1, 2, 3, 4, 5, 6, 7, 8, or $9\times10^{-8}$ molar concentrations. In other embodiments, the Httn proteins may be used at or about 1, 2, 3, 4, 5, 6, 7, 8, or $9\times10^{-7}$ molar concentrations. In other embodiments, the Httn proteins may be used at or about 1, 2, 3, 4, 5, 6, 7, 8, or $9\times10^{-6}$ molar concentrations. In other embodiments, the Httn proteins may be used at or about 1, 2, 3, 4, 5, 6, 7, 8, or $9\times10^{-5}$ molar concentrations. In other embodiments, the Httn proteins may be used at or about 1, 2, 3, 4, 5, 6, 7, 8, or $9\times10^{-4}$ molar concentrations. In other embodiments, the Httn proteins may be used at or about 1, 2, 3, 4, 5, 6, 7, 8, or $9\times10^{-3}$ molar concentrations.

In another embodiment, gel electrophoresis is used to identify Httn aggregates. Gel electrophoresis can identify Httn aggregates and may be detected by western blot or other well-known visualization or quantification techniques. Other embodiments for quantification include, filter trap and ELISA assays. In preferred embodiments, quantification may make use of trapping the Httn proteins with molecules that specifically bind it, such as anti-polyglutamine antibodies (see below). Other assays contemplated by the invention include XTT cell rescue assays and Flow cytometry.

The quantitation steps in the methods disclosed herein may require one or more antibodies, derivatives, or antibody-like molecules. In one embodiment, antibodies directed to epitopes on the Httn molecule may be used. In a preferred embodiment, a monoclonal antibody is used. In another preferred embodiment, an immunoglobulin protein that specifically binds an epitope on Httn is used. In a most preferred embodiment, the mAb1574 monoclonal antibody is used.

The term antibody is meant to include monoclonal antibodies, polyclonal antibodies, antibodies, antibody fragments (e.g., Fc domains), Fab fragments, single chain antibodies, bi- or multi-specific antibodies, Llama antibodies, nano-bodies, diabodies, Fv, Fab, F(ab')2, Fab', scFv, scFv-Fc, and the like. Also included in the term are antibody-fusion proteins, such as Ig chimeras.

The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region. "Antibody fragments" comprise a portion of an intact antibody, preferably comprising the antigen binding region thereof. Examples of antibody fragments include Fab, Fab', F(ab')2, and Fv fragments; diabodies; linear antibodies; single-chain antibody molecules; and multispecific antibodies formed from antibody fragments. The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies.

In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

Antibodies that bind specifically to an antigen have a high affinity for that antigen. Antibody affinities may be measured by a dissociation constant (Kd). In certain embodiments, an antibody provided herein has a dissociation constant (Kd) of ≤100 nM, ≤10 nM, ≤1 nM, ≤0.1 nM, ≤0.01 nM, or ≤0.001 nM (e.g. $10^{-8}$M or less, e.g. from $10^{-8}$ M to $10^{-13}$M, e.g., from $10^{-9}$M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 μM or 26 μM [125I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using, for example, surface plasmon resonance assays using a BIACORE®-2000 or a BIACORE®-3000 (BIAcore, Inc., Piscataway, N.J.) at 25° C. with, e.g., immobilized antigen CM5 chips at ~10 response units (RU). An exemplary protocol follows: Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon See, e.g., Chen et al., J. Mol. Biol. 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette. Other coupling chemistries for the target antigen to the chip surface (e.g., streptavidin/biotin, hydrophobic interaction, or disulfide chemistry) are also readily available instead of the amine coupling methodology (CM5 chip) described above, as will be understood by one of ordinary skill in the art.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al, Nature, 256: 495 (1975); Harlow et al, Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995). The above patents, publications, and references are incorporated by reference in their entirety.

In order that the invention described herein may be more fully understood, the following examples are set forth. It should be understood that these examples are for illustrative purposes only and are not to be construed as limiting this invention in any manner.

Example 1: Collection of Human Cerebral Spinal Fluid (CSF) Samples and Use in Cell Cultures Human CSF from HD patients and non-HD individuals was obtained and then frozen at −80 degrees. Prior to the assay, thawed CSF samples were added to cell cultures in culture medium. The final CSF dilution was 3:100 in the culture medium. RGC5 and SH-SY5Y were grown in DMEM plus10% FBS. PC12 cells were grown in MEM/F12 with 10% horse serum and 5% FBS, 200 µg/ml Zeocin, and 50 µg/ml G418). Postmortem CSF were obtained from the UCLA CSF Tissue Bank. PREDICT CSF samples were provided by Coriell Institute for Medical Research. The dementia and control CSF were a gift from Dr. John Ringman at UCLA. They were prepared as follows: Lumbar punctures were performed using 22 (gravity drainage) or 24 gauge (aspiration via syringe) atraumatic Sprotte needles. Collected CSF was spun at 2620 rpms for 15 minutes and then aliquoted into 500 microliter polypropylene tubes, frozen and stored at −80 degrees centigrade within 2 hours. BAC HD samples were obtained from CHDI.

The media with 1% CSF was added to Httl4A2.6 inducible PC12 cell cultures (Apostol et al., Proc. Nat'l. Acad. Sci. USA 100(10):5950-55(2003), incorporated by reference herein in its entirety). Httl4A2.6 inducible PC-12 cells express a truncated form of an expanded repeat Httn exon 1 protein (SEQ ID NO:1) fused at the C-terminus to enhanced green fluorescent protein (EGFP, N17-103Q-EGFP, no proline-rich region, sequence not shown). 14A2.6 cells were induced with 2.0 or 2.5 µM Ponasterone A (PA). PA is an inducer of the HTT gene and the additional Httn protein expression leads aggregation.

Example 2: Detecting Huntingtin Protein Using Dot Blot Assay

Figure 2:
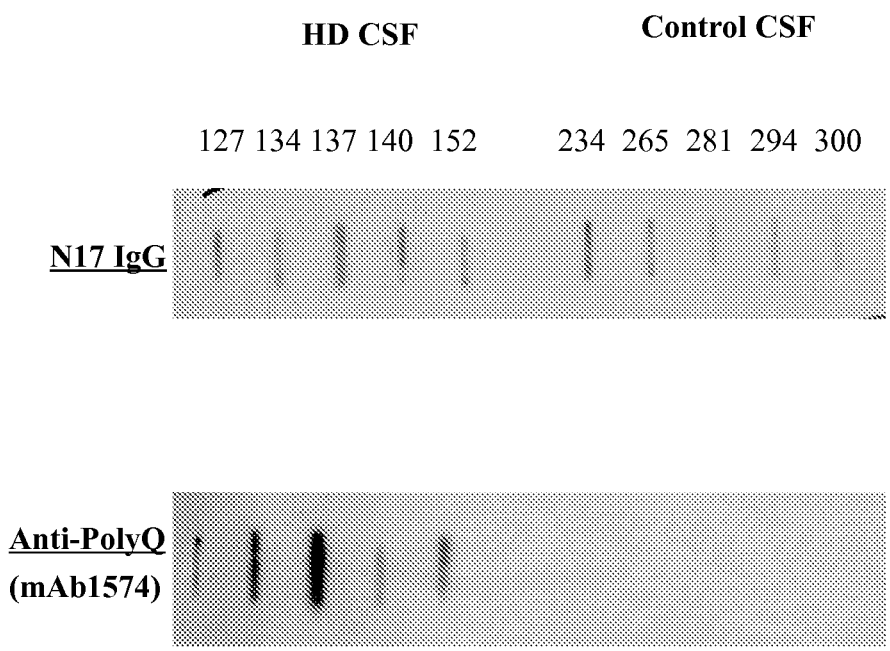
FIG. 2. Results of dot blot assays that show that polyglutamine Httn variants in the CSF from HD but not normal subjects caused increased amounts of Httn aggregates in the cells of the assay.
Figure 3A:
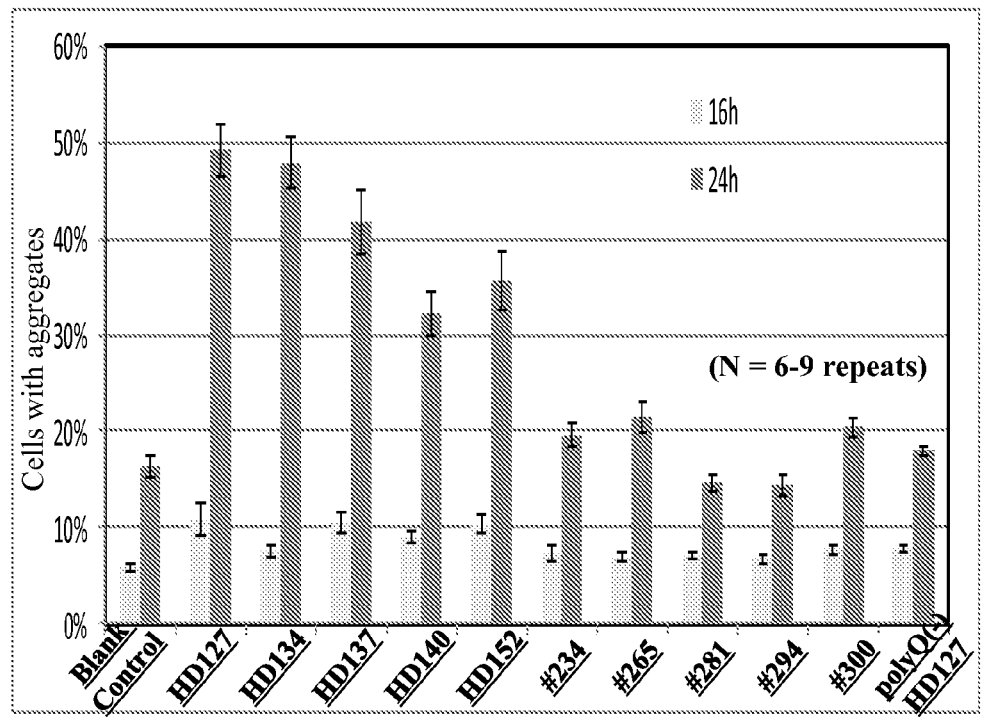
FIG. 3. (a) Fluorescence microscopy assays showing that polyglutamine Httn variants in the CSF from HD but not normal subjects caused Httn aggregation in the cells of the assay. (b) Fluorescence microscopy assays showing increased percentage of cells with mHttn aggregates and increased amount of Httn aggregates with GFP tags following oligomeric polyQ seeding. Immunodepletion of Httn in HD CSF decreases percentage of cells with aggregates (not shown).

Httn protein was visualized using a dot blot assay. Briefly, the medium was removed from the cells and they were washed. Next the cells were lysed and bound to nitrocellulose or PVDF paper and washed. The bound samples were then exposed to an antibody directed to the N17 portion of Httn which is present in both HD and non-HD patients. In parallel, bound samples were exposed to the anti-polyglutamine (PolyQ) antibody mAb1574. The samples were washed and counterstained with an anti-IgG antibody bearing a chromophore. The filters were washed and visualized by autoradiography. (FIG. 2). Alternatively, the proteins were visualized by enhanced chemiluminescence (ECL, Amersham). In non-HD CSF, normal Httn was detected. In the HD CSF, there was an expanded polyglutamine protein that was detected and not found in the non-HD CSF. The mHttn in the HD CSF was decreased by the addition of anti-polyQ antibodies to the CSF prior to the assay. (FIG. 3a, last data set). The results show, for the first time, that both normal and expanded Httn in CSF can be detected and monitored using antibodies.

Httn and mHttn protein from human blood plasma is also visualized using the steps described above.

Example 3: Diagnostic Assay for Huntington's Disease Using GFP Fluorescence Microscopy The Httn aggregates were also quantified using GFP fluorescence as described in Sontag et al., Proc. Nat'l Acad. Sci. USA 110(8):3077-82 (2013) (incorporated herein by reference in its entirety). Briefly, 14A2.6 cells were grown as on UV-treated coverslips for 24 h and then induced with 2.0 or 2.5 μM PA for 16 or 24 hours. Cells were then fixed in 2% paraformaldehyde, permeabilized with 0.1% Triton X-100 in PBS, and nuclei were stained with 4',6-diamidino-2-phenylindole. Fluorescent microscopy was performed using Axiovision software and a Zeiss AxioObserver.Z1 microscope. A minimum of 500 cells were counted from ~5-6 fields in three independent experiments for each data point at 20× magnification. Aggregation is expressed as the percentage of cells with visible inclusions versus total number of cells. As shown in FIG. 3a, CSF taken from the Huntington's patients (HD127, HD134, HD137, HD140, and HD152) induced significantly more cells to form aggregates than the control CSF samples. Additionally, when anti-polyQ antibody was added to a test sample of HD127, the increased aggregation was ablated. These results were demonstrated in several inducible cell lines including 14A2.6 PC-12 cells, transfected RGC5 ganglion cells, and transfected SH-SY5Y neuroblastoma cells. Thus, the CSF from HD patients significantly enhanced the presence of Httn aggregates as compared to the CSF obtained from non HD individuals. Httn and mHttn protein from human blood plasma is also visualized using the steps described above.

Figure 3B:
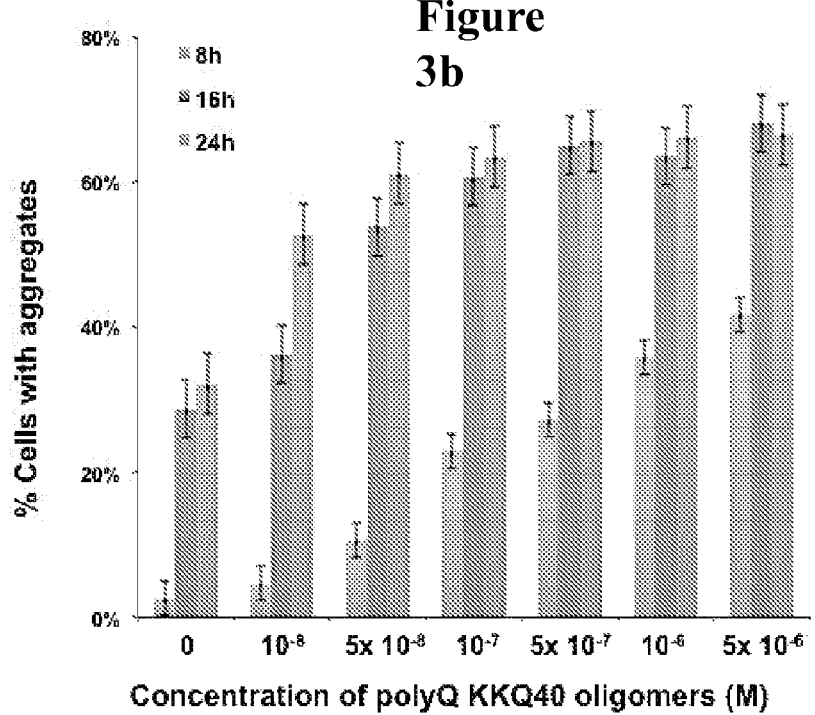

An inducible PC12 cell model of HD (Httl4A2.6), which stably expresses enhanced green fluorescence protein (GFP)-tagged mHtt exon 1 protein (mHttex1-GFP) following Ponasterone A induction, was used as described in Apostol et al., Proc. Nat'l Acad. Sci. USA 100 (2003), incorporated herein by reference in its entirety. FIG. 3b shows that the formation of intracellular mHttex1 aggregates in cultured Httl4A2.6 cells was significantly increased using polyQ seeds starting at 10 nM. This was shown both as the percentage of cells with aggregates and the abundance of insoluble aggregates measured by filter retardation-GFP immunoblotting assay. Filter retardation was performed according to Wanker, et al. *Methods in Enzymology* 309, 375-386 (1999), incorporated herein by reference in its entirety. Briefly, following the cell-free assays, 800 μl 2% SDS PBS was added to each tube. Diluted samples were directly filtered on 0.2 μm nitrocellulose membranes and washed twice with 2 ml of 2% SDS PBS using a manifold vacuum dot blotter. The membranes were subsequently blotted with anti-GFP antibodies following a Western blot procedure.

Example 4: In Vitro Diagnostic Assay for Huntington's Disease

Figure 4:
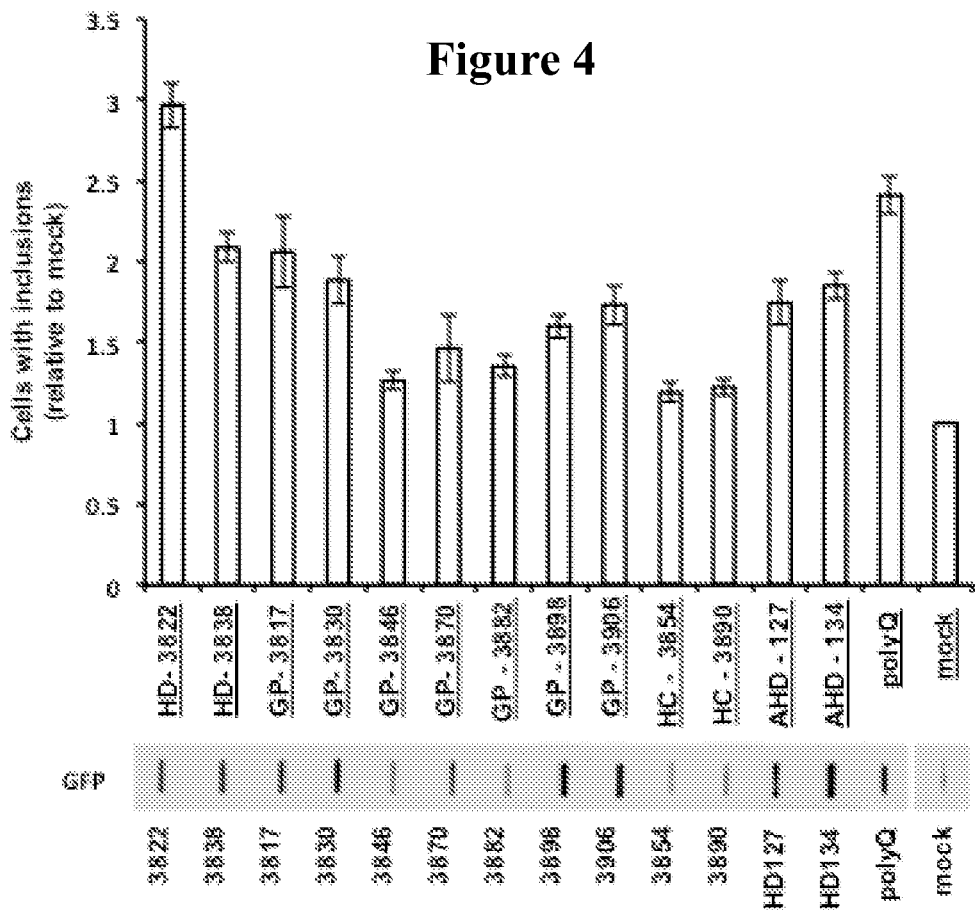
FIG. 4. Differential seeding using CSF samples from living PREDICT subjects with clinical HD, gene positive subjects in which clinical motor symptoms have not developed, and controls. The graph shows the percentage of cells with aggregates and the blot shows the amount of mHTT aggregates.

An extremely sensitive cell-free diagnostic assay was developed. mHttex1 aggregation was enhanced to a surprisingly high level by exogenous polyQ oligomers. mHttex1 aggregation was observed in cell lysates (supernatants) prepared from Httl4A2.6 cells expressing mHttex1-GFP following Ponasterone A induction. Notably, an increased signal for seeded aggregation was detected starting at $10^{-12}$ M (1 pM), $10^4$ times lower than the lowest dosage used in cell-based assay (FIG. 4). Importantly, fluorescent microscopy demonstrated direct association of Cy3-labeled polyQ seeds with mHttex1-GFP in aggregates formed in the cell-free mixture for the aggregation assay (data not shown). Newly seeded aggregation of mHttex1 by polyQ oligomers were also confirmed by agarose gel electrophoresis followed by Western blotting using a GFP-specific antibody as described previously (not shown). Miller et al., *Proc. Nat'l Acad. Sci. USA* 107, 14128-14133 (2010); Zhang et al. *Proc. Nat'l Acad. Sci. USA* 106, 4653-4658 (2009); Sontag et al., *Proc. Nat'l Acad. Sci. USA* 110(8):3077-82 (2013). The foregoing are incorporated by reference herein in their entirety.

Oligomeric seeds: polyQ seeds were prepared from synthetic peptide of KKQ4OKK (SEQ ID NO:2) as described previously. Chen & Wetzel, *Solubilization And Disaggregation Of Polyglutamine Peptides. Protein Science: A Publication of the Protein Society* 10, 887-891, (2001), incorporated herein by reference in its entirety. HiLyte Fluor 647-labeled and unlabeled human $A\beta_{1-40}$ and $A\beta_{1-42}$ peptides were purchased from AnaSpec (Fremont, Calif.) and preformed Aβ oligomers were prepared as described. Kayed et al., *Science* 300(5618):486-9 (2003). The foregoing are incorporated herein by reference in their entirety.

Cell free aggregation assay: Httl4A2.6 cells which were grown in medium containing 2 μM ponasterone A for 10~12 hr and induced expression of mHttex 1-GFP but no visible intracellular aggregates were harvested, rinsed, homogenized in cold PBS containing protease inhibitor cocktail, centrifuged at 16,000×g for 30 min at 4 C twice. Total protein concentrations of supernatants were calibrated using the Sigma-Aldrich total protein assay kit following vendor's instruction. An aliquot of 100 μg total protein of the supernant, preformed oligomeric seeds or CSF samples were mixed together to make a final volume of 25 μl in an Eppendorf tube for incubation at RT in dark for 16 hr. Aggregates formed in the cell free assays were then measured by filter retardation assay.

Example 5: Aggregation from Seeding is Specific to mHtt

Aggregation of mHttex1 is specific to mHtt because it did not occur with proteins other than mHtt. Httl4A2.6 cells were treated with 0.5 μM of Aβ1-40, Aβ1-42, alpha-synuclein, and A53T alpha-synuclein, Alzheimer's disease (AD), and Parkinson's disease—associated oligomers, in the same manner as polyQ seeds. No significant enhancement of intracellular mHttex 1-GFP aggregates was detected (data not shown). Confirming results were obtained from filter retardation-GFP immunoblotting following cell-free aggregation assays; no notable changes in mHttex1 aggregation were found in the cell lysates with up to 5 μM of Aβ1-40, Aβ1-42, alpha-synuclein, and A53T alpha-synuclein oligomeric seeds (data not shown). These observations were further corroborated by the total internal reflection microscopy (TIRF) single molecule imaging results based on photobleaching of mHttex1-GFP aggregates formed in Httl4A2.6 lysates seeded with either AlexFlour647-conjugated polyQ or Aβ1-42 oligomers (data not shown). In contrast to the polyQ oligomers, which were mostly linked with mHttex1-GFP aggregates from photobleaching imaging, few labeled Aβ1-42 oligomers overlapped with GFP fluorescence from the mHttex1-GFP aggregates.

A significant increase in newly formed mHttex1 aggregates was consistently found in Httl4A2.6 cell lysates seeded with HD CSF samples but not with CSF from non-HD subjects. CSF from gene positive subjects who have not yet developed clinical motor symptoms revealed a range of seeding results from HD to non-HD measures. FIG. 4 shows the relative levels of cells with mHtt aggregates (bars) and amount of aggregate protein with GFP tags (GFP panel) following seeding with CSF from blinded PREDICT samples with autopsy HD and polyQ control subjects.

Increased aggregates were present in Huntington's Disease subjects that showed clinical motor symptoms (HD), gene-positive subjects without clinical symptoms (GP), and autopsy HD subjects (AHD). Healthy controls (HC) did not show increased aggregates. These results demonstrate how CSF seeding is used to measure Huntington's Disease progression.

```
SEQ ID NO: 1 is a truncated Httn protein:
MATLEKLMKA FESLKSFQQQ QQQQQQQQQQ QQQQQQQQQQ
QQQQQQQQQQ QQQQQQQQQQ QQQQQQQQQQ QQQQQQQQQQ
QQQQQQQQQQ QQQQQQQQQQ QQQQQQQQQQ QQQQQQQQQ SEQ ID NO: 2 is a synthetic Httn peptide
oligomer:
KKQQQQQQQQ QQQQQQQQQQ QQQQQQQQQQ QQQQQQQQQQ
QQKK
```

All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

---

What is claimed:

1. A method for monitoring the severity of Huntington's Disease (HD) in a subject, comprising;
   a. exposing a first cell culture having cells that express a human Huntingtin (Httn) protein variant comprising SEQ ID NO:1 that aggregates through its poly-glutamine domain to a bodily fluid taken from said subject with HD;
   b. quantifying the Httn variant aggregates in said first cell culture;
   c. exposing a second cell culture having cells that express said Httn protein variant that aggregates through its poly-glutamine domain to a negative control sample;
   d. quantifying the Httn variant aggregates in said second cell culture;
   e. comparing the quantity of variant Httn aggregates in said first and said second cell cultures;
wherein a larger quantity of Httn variant aggregates in said first cell culture as compared to said quantity of aggregates in said second cell culture indicates a severity of said Huntington's Disease, wherein said negative control sample is derived from non-HD cerebrospinal fluid (CSF), saline, solvents, diluents, or water.

2. The method of claim 1, wherein said bodily fluid is CSF or blood plasma.

3. The method of claim 1, wherein said first cell culture and said second cell culture comprise cells that are derived from a mammal, fish, insect, mold, yeast, bacterium, or archaebacterium.

4. The method of claim 1, wherein said first cell culture and said second cell culture that express said Httn variant comprise cells that are selected from the group consisting of PC-12 cells, RGC5 cells, and SH-SY5Y cells.

5. The method of claim 1, wherein said quantifying step is accomplished by a technique selected from the group consisting of fluorescence microscopy, gel electrophoresis, western blot, dot blot, filter trap, XTT cell rescue, flow cytometry, ELISA, FRET, mass spectroscopy, resonant mass measurement, microfluidic imaging, Archimedes, fluorescence spectrometry, and optical density measurement.

6. The method of claim 5, wherein said quantifying step comprises the use of an antibody that specifically binds said Httn protein variant.

7. A method of determining the progression or regression of HD disease in a subject, comprising repeating the method of claim 1 one or more times to track said severity of said HD disease over time.

8. A method of determining the therapeutic efficacy of a compound for treating HD disease, comprising repeating the method of claim 1 one or more times to track the effect of said compound on said subject over time.

9. A method for monitoring the severity of Huntington's Disease (HD) in a subject, comprising;
   a. exposing a first cell-free composition comprising (i) a human Httn protein variant comprising SEQ ID NO:1, or (ii) a synthetic Httn peptide oligomer comprising SEQ ID NO:2, wherein said human Httn protein variant or said synthetic Httn peptide oligomer aggregate through its poly-glutamine domain to a bodily fluid taken from said subject with HD;
   b. quantifying the Httn variant aggregates in said first cell-free composition;
   c. exposing a second cell-free composition comprising said Httn protein variant or said synthetic Httn peptide oligomer that aggregates through its poly-glutamine domain to a negative control sample;
   d. quantifying the Httn variant aggregates in said second cell-free composition;
   e. comparing the quantity of variant Httn aggregates in said first and said second cell cell-free compositions;
wherein a larger quantity of Httn variant aggregates in said first cell-free composition as compared to said quantity of aggregates in said second cell-free composition indicates a severity of said Huntington's Disease, wherein said negative control sample is derived from non-HD cerebrospinal fluid (CSF), saline, solvents, diluents, or water.

10. The method of claim 9, wherein said first and second cell-free compositions comprise cell extracts.

11. The method of claim 9, wherein said first and second cell-free compositions comprise said synthetic Httn peptide oligomer.

12. The method of claim 9, wherein said bodily fluid is CSF or blood plasma.

13. The method of claim 10, wherein said first and second cell-free compositions comprising said Httn protein variant or synthetic Httn peptide are lysates or extracts from cells selected from the group consisting of PC-12 cells, RGC5 cells, and SH-SY5Y cells.

14. The method of claim 9, wherein said Httn variant further comprises a fluorescence tag.

15. The method of claim 9, wherein said quantifying step is accomplished by a technique selected from the group consisting of fluorescence microscopy, gel electrophoresis, western blot, dot blot, filter trap, XTT cell rescue, flow cytometry, ELISA, FRET, mass spectroscopy, resonant mass measurement, microfluidic imaging, Archimedes, fluorescence spectrometry, and optical density measurement.

16. The method of claim 15, wherein said quantifying step comprises the use of an antibody that specifically binds an Httn protein variant.

17. A method of determining the progression or regression of HD disease in a subject, comprising repeating the method of claim 9 one or more times to track said severity of said HD disease over time.

* * * * *

SEQUENCE LISTING

```
<160> NUMBER OF SEQ ID NOS: 2

<210> SEQ ID NO 1
<211> LENGTH: 119
<212> TYPE: PRT
<213> ORGANISM: Homo sapiens

<400> SEQUENCE: 1

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
            20                  25                  30

Gln Gln Gln Gln Gln Gln Gln Gln Gln Gln Gln Gln Gln Gln Gln Gln
        35                  40                  45

Gln Gln Gln Gln Gln Gln Gln Gln Gln Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Gln Gln Gln
                85                  90                  95

Gln Gln Gln Gln Gln Gln Gln Gln Gln Gln Gln Gln Gln Gln Gln Gln
            100                 105                 110

Gln Gln Gln Gln Gln Gln Gln
        115

<210> SEQ ID NO 2
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Lys Lys Gln Gln Gln Gln Gln Gln Gln Gln Gln Gln Gln Gln Gln Gln
1               5                   10                  15
```

```
Gln Gln Gln Gln Gln Gln Gln Gln Gln Gln Gln Gln Gln Gln Gln
                20                  25                  30
Gln Gln Gln Gln Gln Gln Gln Gln Gln Gln Lys Lys
            35                  40
```